United States Patent [19]

Bistrian

[11] Patent Number: 5,081,105
[45] Date of Patent: Jan. 14, 1992

[54] METHOD OF TREATING CANCER USING STRUCTURED LIPIDS

[75] Inventor: Bruce R. Bistrian, Ipswich, Mass.

[73] Assignee: New England Deaconess Hospital Corporation, Boston, Mass.

[21] Appl. No.: 470,164

[22] Filed: Jan. 25, 1990

Related U.S. Application Data

[63] Continuation-in-part of Ser. No. 144,930, Jan. 15, 1988, Pat. No. 4,906,664.

[51] Int. Cl.$^5$ .................... A61K 37/00; A61K 31/22; A61K 31/23
[52] U.S. Cl. ...................................... 514/2; 514/549; 514/552
[58] Field of Search ............... 514/552, 557, 558, 560, 514/549, 2

[56] References Cited

U.S. PATENT DOCUMENTS

| | | | |
|---|---|---|---|
| 4,528,197 | 7/1985 | Blackburn | 514/552 |
| 4,607,052 | 8/1986 | Mendy et al. | 514/547 |
| 4,703,062 | 10/1987 | Blackburn et al. | 514/552 |
| 4,906,664 | 3/1990 | Bistrian et al. | 514/552 |

OTHER PUBLICATIONS

*The Handbook of Chemistry and Physics,* 57th ed., CRC Press, pp. D216-217, Weast, Ed.
"Fish Oil Slows Tumor Growth and Prolongs Survival in a Transplantable Metastatic Breast Cancer Model", (ABSTRACT) Szeluga et al., Metabolism Lab., NEDH, Harvard Medical School, Boston, Mass.
"Medium-chain triglycerides: an update", Bach and Babayan, Amer. J. of Clin. Nut., 36:Nov. 1982, pp. 950-962.
"Improved protein kinetics and albumin synthesis by branched chain amino acid-enriched total parenteral nutrition in cancer cachexia", Tayek et al., CANCER 58:No 1, Jul. 1, 1986.
"Some practical and theoretic concepts in the nutritional assessment of the cancer patient", Bistrian, CANCER, 58:No. 8, Oct. 15, 1986.
"Effect of total enteral nutrition with structured lipid on protein metabolism in thermally injured rats", DeMichele et al., Fed. Proc., 46:1086 (1987).

*Primary Examiner*—Frederick E. Waddell
*Assistant Examiner*—Raymond J. Henley, III
*Attorney, Agent, or Firm*—Lahive & Cockfield

[57] ABSTRACT

Disclosed is a method of treating cancer using nutritional support therapy by administration of a structured lipid containing both $\omega$3 fatty acids and medium-chain fatty acids. The therapy may be used as total parenteral nutrition or as a nutritional supplement. The addition of tumor necrosis factor may also be beneficial.

6 Claims, No Drawings

METHOD OF TREATING CANCER USING STRUCTURED LIPIDS

REFERENCE TO RELATED APPLICATION

The present application is a continuation-in-part of U.S. Pat. Application Ser. No. 4,906,664, issued Mar. 6, 1990, entitled "Nutritional Supplement for Treatment of Cancer Cachexia," filed Jan. 15, 1988 now U.S. Pat. No. 4,906,664 issued Mar. 6, 1990, the disclosure of which is incorporated herein by reference.

BACKGROUND OF THE INVENTION

The present invention relates to the treatment of cancer with a parenteral nutritional supplement, particularly a supplement having a specific class of structured lipids as its primary fat source. Surprisingly, the supplement containing these structured lipids, when used as part of a total parenteral nutrition diet, has been shown to modify tumor growth rate, tumor fractional synthetic rate, and tumor protein breakdown rate. As indicated by the previously cited U.S. Pat. No. 4,906,664, the same structured lipids are also useful in the treatment of cancer cachexia, the fasting-like state associated with certain forms of cancer.

Total parenteral nutrition, as well as parenteral nutritional supplements, are often used in the treatment of critically ill patents to provide necessary fats and other calorie sources required for survival of the patient. Heretofore, these supplements have been considered useful solely to ameliorate the physiologic loss of nutrients in patients such as those having undergone surgery or cancer therapy. Although certain medium-chain triglycerides and structured lipids, including some containing medium-chain triglycerides, have been shown to have benefits in treating hypercatabolic patients, see U.S. Pat. No. 4,528,197, assigned to KabiVitrum, Inc.; DeMichele et al., "Effective Total Enteral Nutrition with Structured Lipids on Protein Metabolism in Thermally Injured Rats," Fed.Proc. 46:1086 (1987); Bach and Babayan, "Medium-Chain Triglycerides: Update," Am.J.Clin.Nutrition 36:950-962 (November 1982); and U.S. Pat. No. 4,703,062, assigned to Baxter-Travenol, Inc., no work was published describing the effects of using structured lipids as a cancer cachexia treatment before the filing of the aforementioned U.S. Pat. No. 4,906,664.

While some of the work described in these papers concerned the effects of medium-chain triglycerides and structured lipids on ill or stressed patients, there was nothing to suggest that a change in the fat content of the diet could actually affect cancerous tumor growth rates and/or protein metabolism in the tumors. Even the early work on the family of structured lipids used in the present invention, see U.S. Pat. No. 4,871,768, gave no indication of the beneficial effects of this family of structured lipids in cancer treatment. In fact, early tests to determine if a change in nutritional lipids can affect a cancer treatment, Crosby et al., "Effect of Structured Lipid-Enriched Total Parenteral Nutrition in Rats Bearing Yoshida Sarcoma," J.Nutritional Biochemistry (In Press) indicated that there was no improvement in terms of tumor growth rate or fractional synthetic rate by a modification in the parenteral diet from classic long-chain triglyceride (LCT) mixtures of soybean oil and safflower oil to the structured lipids. However, this early work was carried out using structured lipids having medium-chain and long-chain ω6 fatty acids, not ω3 fatty acids. In contrast, the present invention requires that as a statistical average, both the medium-chain fatty acids and the ω3 fatty acid be on the same structured lipid.

Until the experiments which lead to the present invention was carried out, even those involved in the test program did not believe that the structured lipids would have any effect on cancer. A 1986 article by one of the inventors, Bistrian, "Some Practical and Theoretical Concepts in Nutritional Assessment of the Cancer Patient," CANCER 58(8):1863-1866 (1986) did not even theorize that a change in parenteral nutrition could modify tumor growth rate but rather merely suggested that there was some parallel between hypercatabolic states and cancer cachexia, the fasting-like state often associated with cancer. There was no inkling whatsoever that diet modification could reduce the tumor growth rate or otherwise affect the cancer itself as compared with the cachectic state associated with it.

Accordingly, an object of the invention is to provide a lipid-based diet or nutritional support which can treat cancer.

Another object of the invention is to provide a nutrition supplement which can affect cancer tumor growth rate.

A further object of the invention is to provide total parenteral nutrition for the treatment of cancer.

These and other objects and features of the invention will be apparent from the following description.

SUMMARY OF THE INVENTION

The present invention features a method of treating cancer with nutritional support or therapy. The method is based, in part, on the discovery that certain structured lipids, either alone or together with tumor necrosis factor, cause a dramatic decrease in tumor growth rate upon administration to patients.

The method of the invention includes the steps of administering, a diet, e.g., a parenteral nutrition diet, having a certain class of structured lipids as its primary lipid source. The structured lipid has the formula

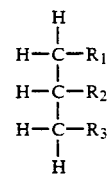

where one of $R_1$, $R_2$ and $R_3$ is a medium-chain fatty acid or an active derivative thereof, a second of $R_1$, $R_2$ and $R_3$ is ω3 fatty acid or an active derivative thereof, and the third one of $R_1$, $R_2$ and $R_3$ is selected from the group consisting of H, OH, short, medium and long-chain fatty acids, and active derivatives thereof.

As used herein, the term "active derivative" means and includes esters, ethers, amides, and metal salts of the fatty acids. The derivatives are active because they will provide a qualitative improvement in nutritional benefit similar to that obtained from the use of fatty acid itself.

The diet preferably further includes nutritionally sufficient sources of carbohydrates, amino acids, e.g., proteins, and vitamins. Those skilled in the art are familiar with the requirements for carbohydrates, amino acids, and vitamins for inclusion in parenteral or enteral nutrition. The diet most preferably is used in the form of total parenteral nutrition.

The most preferred structured lipids have short, medium-chain, or ω3 fatty acids, or their active derivatives, as the third one of $R_1$, $R_2$ and $R_3$. Most preferably, the ratio of medium-chain fatty acids to ω3 fatty acids is about one-to-one. Further, as used herein, the term "short-chain fatty acids" means fatty acids with less than 8 carbons in the carbon backbone, the term "medium fatty acids" means molecules with 8-12 carbons on the fatty acid backbone, and the term "long-chain fatty acid" means molecules with greater than 12 carbons on the fatty acid chain. The long-chain fatty acids are classified into categories which include the ω3 fatty acids (C—:—ω3) and the ω6 fatty acids (C—:—ω6). Oils which provide high content of ω3 include most fish oils such as tuna, menhaden, sardine, and anchovy as well as certain plant oils. The ω6 oils are the more commonly used oils and include those from safflower oil, soybean oil and other polyunsaturated oils.

In one embodiment of the invention, the structured lipid is infused together with tumor necrosis factor to form a hybrid parenteral infusion. Although tumor necrosis factor and the structured lipid of the invention individually will reduce tumor growth rate, the combination, whether given in a single supplement or in close time proximity, seems to be even better than either individual component.

The following description and the Examples will further illustrate the invention.

DETAILED DESCRIPTION OF THE INVENTION

The structured lipids of the invention provide clearly demonstrable benefits in treatment of cancer as compared with classic long-chain triglyceride parenteral nutrition supplements as well as other structured lipid nutritional diets. The following non-limiting Examples will further clarify and illustrate the present invention.

EXAMPLE 1

A. Experimental Procedure

The following general experimental procedure was used for all of the Examples. Male Sprague-Dawley rats weighing approximately 45 g were broken into two groups; one group was inoculated with $10^7$ cells of viable Yoshida sarcoma into the subcutaneous area of the right flank, and the other group received an identical injection of sterile saline. The animals were weighed, returned to their cages, and allowed to continue standard laboratory chow and tap water for 7 days. The rats bearing the rapidly growing tumors (Yoshida sarcoma) had diminished appetites and when re-weighed at day 7 were significantly lighter than the nontumor-bearing animals, indicating their cachectic state.

At day 7, all the rats were anaesthetized and a silastic catheter was inserted through the internal jugular vein. The animals were randomly divided into groups and were administered total parenteral nutrition through the catheter.

Table I lists the materials in the tested dietary composition in terms of amino acids, glucose and lipids administered to all the animals. These values are standard for a dietary composition.

TABLE I

| DIETARY COMPOSITION | | | |
|---|---|---|---|
| Amino Acids | Glucose | Lipid | Total |
| kcal/kg.BW | kcal/kg.BW | kcal/kg.BW | kcal/kg.BW |
| 50 (22%) | 85 (39%) | 85 (39%) | 220 |
| Additives per 1000 ml: | | | |
| NaCl | | 30 mEq | |
| NaAc | | 30 mEq | |
| KCl | | 30 mEq | |
| KAc | | 25 mEq | |
| KPhos | | 16 mEq | |
| Ca + Gluconate | | 8.5 mEq | |
| MgSO$_4$ | | 8.0 mEq | |
| Trace minerals | | 10.2 mEq | |

0.5 ml of MVC 9 + 3 vitamins and 0.25 ml of choline chloride (30% w/v) were added per 100 ml of hyperal solution.

B. Experimental Specifics

The tumor-containing animals in this Example received lipids either in the form long-chain triglycerides (Liposyn II, a 50-50 mixture of safflower and soybean oil, Abbott Laboratories, North Chicago, Ill.) (the control group) or a structured lipid having a statistical average of 43% medium-chain fatty acids (C8–C12) and 57% long-chain fatty acids (C14–C18) by weight, primarily ω6 fatty acids (the test group). The diets were administered at half the planned rate the first night (day 7–8) to allow for adaption to the glucose and fat and then full caloric intake thereafter. Holter pumps (Critikon, Inc., Tampa, Fla.) were used for infusion of the diet through the catheter and the infusion rate was adjusted so each animal received approximately 220 calories/kg body weight/day with 2 gm amino nitrogen/kg body weight/day.

On day 10, (1-$^{14}$C)-1-leucine (50mCi/mmol, ICN, Irvine, Calif.) and 6-$^3$H-glucose (Amersham International, Inc., Amersham, U.K.) were added to the diets and a four-hour constant infusion was conducted to investigate protein and glucose kinetics. Each animal received 1.5 μCi/hour of leucine and 14 μCi/hour of glucose at a rate of 1.25cc/hour.

After infusion, the animals were sacrificed by decapitation, the blood was collected in heparinized tubes, and placed on ice. Plasma was separated by centrifugation and stored at $-25°$ C. until the time of analysis. The body was quickly dissected and liver, tumor and portions of the abdominus rectus muscle removed. The muscle, tumor and liver were weighed and stored.

The tumor growth rate was derived by tumor volume measurements on days 7 and 10. Tumor volume measurements were estimated by measurements of tumor length, width and depth. The tumor fractional synthetic rate (FSR) was calculated as a difference between the tumor protein synthesis, measured isotopically, and the tumor growth. The tumor breakdown was measured by assuming that a plateau labelling (steady state) plasma component was achieved when the specific activity maximum was reached in the expired breath.

C. Experimental Results

This experiment, which was used as a control since the structured lipid used was not within the scope of the invention, illustrated that there is substantially no change in tumor growth rate by parenteral infusion of either a structured lipid outside the invention or a long-chain triglyceride. Table II shows the results of this experiment:

TABLE II

|  | STRUCTURED LIPID | LONG CHAIN |
|---|---|---|
| Tumor Growth Rate (%/day) | 32 ± 10 | 33 ± 10 |
| Tumor FSR (%/day) | 50 ± 28 | 68 ± 31 |
| Tumor Breakdown (%/day) | 18 ± 28 | 37 ± 34 |

There is no statistically significant difference among any of these factors.

EXAMPLE 2

In this Example, the same experimental procedures were used except three different lipid infusions were tested. The first lipid infusion was a structured lipid of the invention containing a statistical average of 60 medium-chain fatty acids and 40% menhaden oil by weight which contains primarily $\omega 3$ fatty acids. The second infusion was a control consisting of physical mixture of the medium-chain fatty acids and menhaden oil in the same percentages. The third infusion was a control consisting of a long-chain triglyceride diet, specifically the Liposyn II used in Example 1. The values measured included tumor growth rate, tumor fractional synthetic rate, and tumor protein breakdown. Table III shows the results of these tests.

TABLE III

|  | STRUCTURED LIPID | PHYSICAL MIX | LONG CHAIN |
|---|---|---|---|
| Tumor Growth Rate | 22.4 ± 10.0 | 30.5 ± 10.2 | 31.1 ± 8.8 |
| Tumor FSR | 101.2 ± 42.2 | 42.6 ± 13.6 | 27.5 ± 15.3 |
| Tumor Breakdown | 80.6 ± 46.9 | 12.1 ± 10.6 | −6.8 ± 15.6 |

The differences between the various diets were striking. The tumor fractional synthetic rates and tumor breakdown rates for each of the diets were significantly different with a $P<0.0001$ by diet using an ANOVA test. The tumor growth rate of the physical mix and the long-chain triglycerides were not significantly different from each other but the structured lipid, such as is claimed in the present invention, showed a significant difference from the other two, having a $P<0.05$ using a t-test.

This experiment clearly establishes that the structured lipid of the invention is capable of doing something a classic long-chain triglyceride diet or even a physical mix of the same components cannot do; reduce cancer growth rate.

EXAMPLE 3

In this Example, the same experimental procedures were used as in Examples 1 and 2 except the groups receiving the structural lipid of the invention, and the groups receiving long-chain triglycerides, also received either an infusion of saline (S) or tumor necrosis factor (T) at 20 mcg/kg on days 8 and 9 intravenously. Changes in tumor volume ($\Delta V$), final tumor weight (TW), tumor protein content (TP), changes in body weight ($\Delta BW$), and cumulative nitrogen balance (N) were measured. Table IV illustrates the results of these tests.

TABLE IV

| GROUP | LCT-S | LCT-T | MCT-S | MCT-T |
|---|---|---|---|---|
| $\Delta V$ | 2.26 (1.75) | 0.22 (0.51) | 0.25 (0.42) | −0.08 (1.01)a |
| TW | 4.39 (.83) | 3.12 (.52) | 2.29 (.45) | 2.63 (.75)b |
| TP | 13.93 (.95) | 13.70 (.57) | 15.96 (.70) | 15.81 (.53) |
| $\Delta BW$ | −13.19 (2.84) | −18.91 ((3.61)c | −14.59 (1.96) | −10.75 (1.27) |
| N | 0.28 (.03) | 0.25 (.03) | 0.29 (.02) | 0.37 (0.04) |

The tumor volume as measured by volume change was significantly reduced by feeding either the structured lipid or the tumor necrosis factor, with a $P<0.05$ for either the structured lipid versus LCT or the saline versus the tumor necrosis factor. The tumor weight was also reduced by feeding the structured lipid. The tumor protein content was not changed by a modification of the lipid or the tumor necrosis factor to any significant degree. However, the body weight and nitrogen balance were best maintained in the combined diet having both structured lipid and tumor necrosis factor. Therefore, it appears that there is some interaction or positive benefit by using both the $\omega 3$ fatty acids/medium-chain fatty acid structured lipid diet together with tumor necrosis factor.

The foregoing Examples are purely illustrative and are not intended to be a limitation on the invention. Those skilled in the art can determine other modifications on the formulations used herein.

Such modifications are included within the following claims.

What is claimed is:

1. A method of treating sarcomas in a patient through the use of nutritional support therapy comprising the step of parenterally administering a diet including an effective amount of a structured lipid as its primary lipid calorie source, said structured lipid having the structure

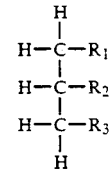

where one of $R_1$, $R_2$ and $R_3$ is a medium-chain fatty acid or an active derivative thereof, a second one of $R_1$, $R_2$ and $R_3$ is $\omega 3$ fatty acid or an active derivative thereof, and the third one of $R_1$, $R_2$ and $R_3$ is selected from the group consisting of H, OH, short, medium and long-chain fatty acids, and active derivatives thereof.

2. The method of claim 1 wherein said diet further comprises nutritionally sufficient sources of carbohydrates, amino acids, and vitamins.

3. The method of claim 2 wherein said diet comprises total parenteral nutrition.

4. The method of claim 1 wherein said third one of $R_1$, $R_2$ and $R_3$ is selected from the group consisting of short-chain fatty acids, medium-chain fatty acids, $\omega 3$ fatty acids, and active derivatives thereof.

5. The method of claim 1 wherein the ratio of medium-chain fatty acids to w3 fatty acids is about 1:1.

6. The method of claim 1 further comprising the step of infusing tumor necrosis factor to said patients.

* * * * *